United States Patent [19]
Davis et al.

[11] Patent Number: 4,859,363
[45] Date of Patent: Aug. 22, 1989

[54] EMULSIONS OF PERFLUOROCARBONS IN AQUEOUS MEDIA

[75] Inventors: Stanley S. Davis, Nottingham; David E. M. Wotton, Bristol, both of United Kingdom

[73] Assignee: I.S.C. Chemicals Limited, London, United Kingdom

[21] Appl. No.: 143,282

[22] Filed: Jan. 7, 1988

Related U.S. Application Data

[63] Continuation of Ser. No. 833,017, Feb. 26, 1986, abandoned.

[30] Foreign Application Priority Data

Feb. 26, 1985 [GB] United Kingdom ................. 8504916

[51] Int. Cl.$^4$ ....................... A61K 9/10; A61K 31/25; B01J 13/00
[52] U.S. Cl. .................................... 252/312; 514/755; 514/832
[58] Field of Search ............... 252/312; 514/755, 832; 570/130

[56] References Cited

U.S. PATENT DOCUMENTS

| | | | |
|---|---|---|---|
| 3,775,489 | 11/1973 | Margrave et al. | 570/130 |
| 3,778,381 | 12/1973 | Rosano et al. | 252/312 X |
| 3,823,091 | 7/1974 | Samejima et al. | 252/312 |
| 3,911,138 | 10/1975 | Clark, Jr. | 514/756 X |
| 3,993,581 | 11/1976 | Yokoyama et al. | 252/312 |

*Primary Examiner*—Richard D. Lovering
*Attorney, Agent, or Firm*—Fleit, Jacobson, Cohn, Price, Holman & Stern

[57] ABSTRACT

Increased stability is conferred on oil-in-water emulsions of perfluorocarbons by addition of a minor (0.1–5% w/v) amount of a fluorinated compound of higher boiling point than the perfluorocarbon being emulsified. The added fluorinated compound is preferably a perfluorinated saturated polycyclic hydrocarbon. The most preferred additive is perfluoroperhydrofluoranthene.

6 Claims, 2 Drawing Sheets

EMULSIONS OF PERFLUOROCARBONS IN AQUEOUS MEDIA

This is a continuation of application Ser. No. 06/833,017, filed Feb. 26, 1986, now abandoned.

This invention relates to emulsions of perfluorocarbons in aqueous media, to provide emulsions suitable for carrying oxygen or other gases, e.g. in an artificial blood application.

It has long been hypothesised that emulsions of certain perfluorocarbons in aqueous media could constitute ideal blood substitutes, chiefly because of their inertness and their ability to transport oxygen and other life-supporting materials around a human or animal body.

Normally such emulsions are formed with the aid of a non-ionic surface-active agent such as those known as polaxamers (as hereinafter defined) or a phosphatide (egg or soy lecithin).

However a problem inherent in such emulsion technology is the tendency of the emulsion to de-stabilize on storage and for the emulsion droplets to grow in size.

For some time, various workers have been studying the properties of perfluorochemicals and their potential use as blood substitutes, not only for blood transfusion but also for tissue oxygenation (cancer chemotherapy), treatment of infarct, as scanning agents in nuclear magnetic resonance, and for the preservation of organ transplants. The literature contains a wealth of information on the preparation of various emulsion systems, the properties of various fluorocarbon liquids and their clearance from the body of animals, as well as some limited clinical studies conducted in Japan and elsewhere. At the present time, the Green Cross Corporation of Japan have available two commercial emulsion systems that seem to show good promise in clinical studies. However a major problem still exists with regard to the stability of emulsions produced with fluorocarbons that have acceptable clearance characteristics.

By far the most information available exists on the material perfluorodecalin. This seems to be ideal in terms of its low biological toxicity as well as its acceptable clearance from the body after administration. Unfortunately this compound does not give emulsions, stable at room temperature for extended periods, without resorting to complex mixtures of emulsifying substances or to mixtures of fluorocarbons. As a consequence, a detailed effort is being made, by various research groups, to produce an emulsion which has better physiological and stability characteristics. In some cases, the physiological requirements have even taken second place to the stability requirement.

We believe that the two aspects of stability and physiological behaviour may not be separable; that is a perfluorocarbon which gives the required physiological effects will, as a consequence, also be somewhat unstable when emulsified, and moreover, that other research groups appear to have considered emulsion stability in a too simplistic way. The major way in which the droplets in emulsions can grow in size is by a process of droplet coalescence. Normally, this can be retarded, and practically eliminated, by using emulsifying agents that can form electrostatic and mechanical barriers at the oil/water interface. However, a much more subtle means of instability can occur in which the small particles become small and the large particles become bigger through a process of molecular diffusion, known as Ostwald ripening (see e.g. Davis et al. (1981) J. Colloid Interface Sci. 80:508).

Molecular diffusion will occur if the oil has a finite solubility in water and if the particles are very small. It will occur even if the droplets have excellent barriers to coalescence but can be prevented in hydrocarbon emulsions using mixed oil systems, that is by the addition of a very small quantity of higher boiling point material (e.g. soyabean oil). Thus, if molecular diffusion is the cause of instability in perfluorodecalin emulsions, attempts at creating even more effective barriers to coalescence will be to no avail. Similar considerations apply to any pure perfluorocarbon system.

DETAILED DESCRIPTION OF THE INVENTION

Figure 1:
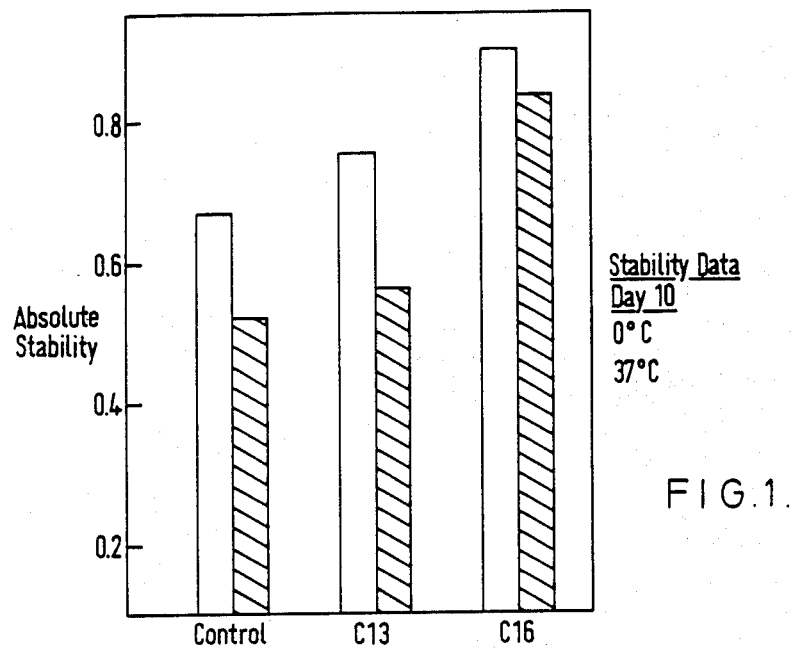
FIGS. 1–4 show the stability of the emulsions as a function of the presence of $C_{13}$ and $C_{16}$ at different times and at different temperatures.

According to the present invention there is provided an oil-in-water emulsion of a perfluorinated hydrocarbon in an aqueous medium, wherein the emulsion is stabilized by the addition of a minor amount of a fluorinated compound of a higher boiling point than the perfluorinated compound being emulsified.

Preferably the fluorinated compound of higher boiling point is a perfluorinated saturated polycyclic hydrocarbon, such as one of the following:

perfluoroperhydrofluorene, $C_{13}F_{22}$
perfluoroperhydrophenanthrene, $C_{14}F_{24}$
perfluoroperhydrofluoranthene, $C_{16}F_{26}$ Of the above, perfluoroperhydrofluoranthene is particularly preferred.

The fluorinated compound of higher boiling point is suitably added in an amount of from 0.1 to 5% (w/v) of the stabilized emulsion, more preferably from 0.5% to 2% (w/v).

The perfluorinated hydrocarbon forming the emulsion is preferably perfluorodecalin.

Other examples of fluorinated compounds of higher boiling point include materials sold under the trade names KRYTOX (RTM) and GALDEN (RTM) (perfluoroethylene oxide/propylene oxide copolymers).

It is believed that the higher boiling component of the emulsion acts to stabilize the composition by dissolving n the fluorocarbon oil and thus by suppressing the destabilizing "Ostwald ripening" effect which is inherent in such an oil-in-water emulsion and gives rise to instability problems in other commercial formulations such as FLUOSOL-DA (RTM).

Preferably the emulsion is formed with the aid of a surface active agent of the poloxamer type. Poloxamers are a class of non-ionic surface active agents being polyoxyethylene-polyoxypropylene-polyoxyethylene block co-polymeric surfactants, sold under the trade name pluronic.

The invention in another aspect provides the use as a blood substitute of an emulsion of a perfluorocarbon in an aqueous medium, according to the first aspect of the invention.

The invention in a further aspect provides a method of stabilizing an oil-in-water emulsion of a perfluorinated hydrocarbon in an aqueous medium, wherein there is added to the said emulsion a minor amount of a fluorinated compound of higher boiling point than the perfluorinated compound emulsified.

The invention will be further described with reference to the following illustrative Examples, which describe the making of typical formulations according to this invention (Examples 1a to 1c), together with the procedure used to test the emulsions for stability (Example 2 and Table 1).

EXAMPLE 1

Preparation of perfluorochemical emulsions with enhanced stability

Emulsions were prepared using an ultrasonic homogeniser (Dawe Soniprobe) (10 minutes homogenisation at setting 5). The formulae were as follows for 50 ml of emulsion:

Example 1a

Perfluorodecalin, 10 ml (20 g)
Pluronic F108 (Poloxamer 388), 1 g
Perfluoroperhydrofluorene, 0.5 ml (1 g)(2% w/v)
Distilled water to 100%, to 50 ml

Example 1b

Perfluorodecalin, 10 ml (20 g)
Pluronic F108 (Poloxamer 338), 1 g
Perfluoroperhydrofluoranthene, 0.5 ml (1 g)(2% w/v)
Distilled water to 100%, to 50 ml

Example 1c

Perfluorodecalin, 10 ml (20 g)
Pluronic F108 (Poloxamer 388) 1 g
Perfluorperhydrophenanthrene, 0.5 ml (1 g)(2% w/v)
Distilled water to 100% to 50 ml Example 1d (Formulation of a control emulsion without added stabilizer)

Perfluorodecalin, 10 ml (20 g)
Pluronic F108 (Poloxamer 388) 1 g
Distilled water to 100%, to 50 ml The boiling points of the fluorinated compounds referred to above are as follows:
Perfluorodecalin, 140°–142° C.
Perfluoroperhydrofluorene, 190°–192° C.
Perfluoroperhydrophenanthrene, 215° C.
Perfluoroperhydrofluoranthene, 242°–244° C.

Example 2

Testing of the perfluorochemical emulsions for stability

The emulsions prepared in Example 1 were stored for a period of 7 days at room temperature and the particle size determined using a Coulter Counter (Model TAII) fitted with a 30 micron orifice tube. The change in the percentage of particles greater than two arbitrary size limits was used as an indicator of stability. The results given in Table 1 below show that the added fluorinated compounds boiling point gave an improved stability to the emulsion system.

TABLE 1

Stability Testing of Fluorocarbon Emulsions
Coulter Counter Analysis: reported as % change in cumulative percentage oversize after 7 days storage at room temperature.

| Example No. | Emulsion type | Change in percentage greater than | |
|---|---|---|---|
| | | 0.83 μm | 1.05 μm |
| 1a | Perfluorodecalin + Perfluoroperhydrofluorene | 0 | −4 |
| 1b | Perfluorodecalin + Perfluoroperhydrofluoranthene | 2 | 1 |
| 1c | Perfluorodecalin + Perfluorperhydrophenanthene | 4 | 2 |
| 1d | Perfluorodecalin alone (as control) | 14 | 10 |

The invention will be further described with reference to the accompanying drawings, wherein FIGS. 1 to 4 are bar charts (histograms) which illustrate the stability of emulsions formed from perfluorodecalin in aqueous media without addition of a higher-boiling component and with the addition of higher-boiling components defined as follows:

C13: Perfluoroperhydrofluorene ($C_{13}F_{22}$)
C16: Perfluoroperhydrofluoranthene ($C_{16}F_{26}$)

In these bar-charts stability is expressed as a fraction of perfect stability (i.e. no separation) which is taken to be unity, the unshaded areas representing the stability of the emulsion at 0° C. and the shaded areas representing stability at 37° C. "Day" represents the day of sizing after preparation of the emulsion.

With reference to the bar charts: FIG. 1 represents stability figures at Day 10 based on emulsions containing:
Perfluorodecalin, 20% (w/v),
Pluronic F-68 (Surfactant), 1% (w/v)
Higher boiling additive, 1% (w/v) (as defined)
Distilled water to, 100% (w/v)

Figure 2:
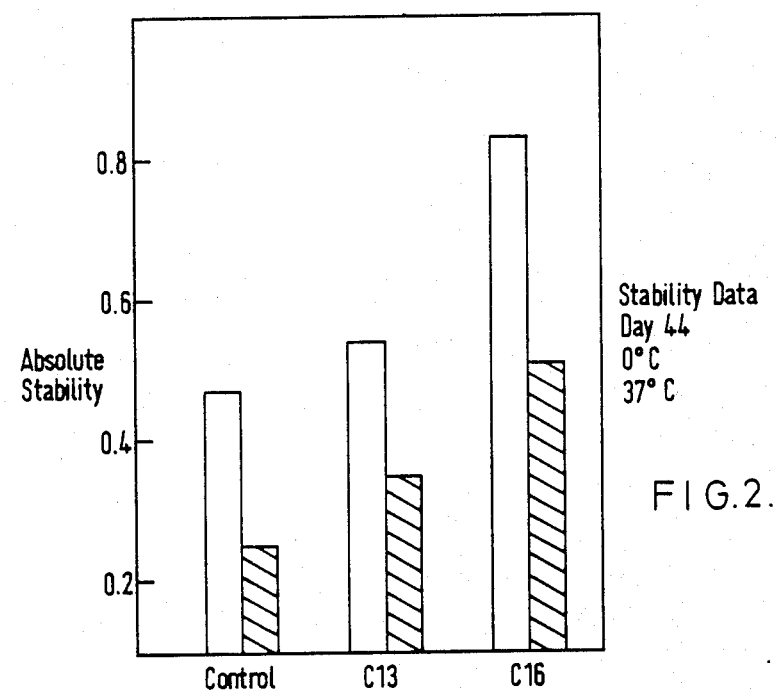

FIG. 2 represents emulsion stability at Day 44 based on emulsions containing
Perfluorodecalin, 20% (w/v)
Pluronic F-68 (Surfactant), 4% (w/v)
Higher-boiling additive, 1% (w/v) (as defined)
Distilled water to, 100% (w/v)

Figure 3:
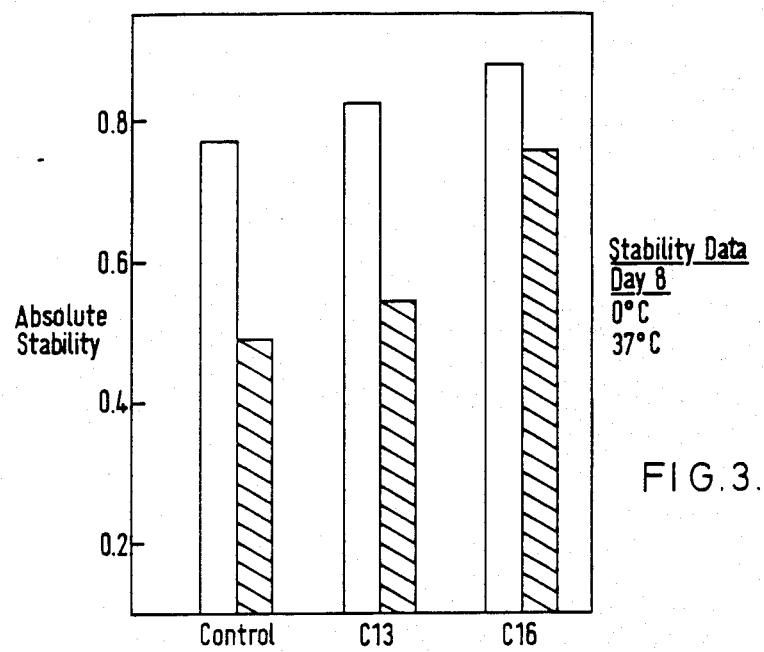

FIG. 3 represents emulsion stability at Day 8 based on emulsions as defined for FIG. 2 above.

Figure 4:
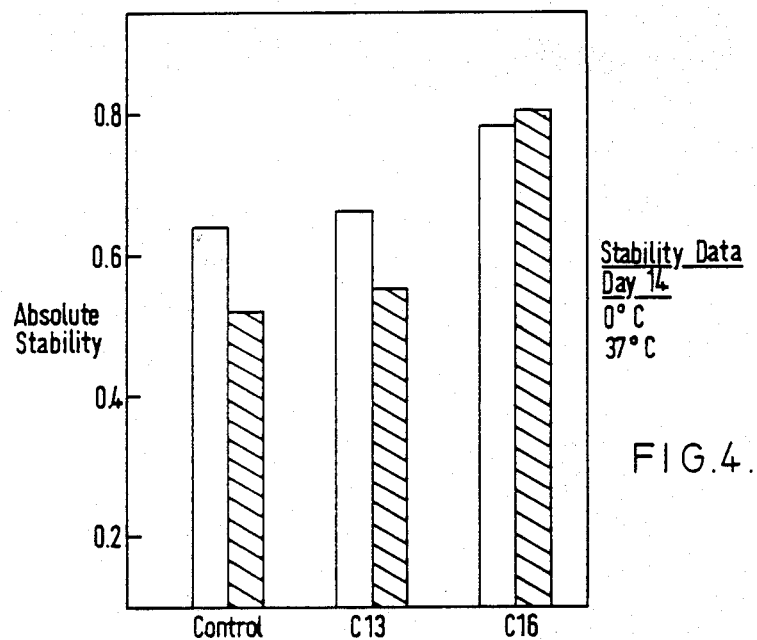

FIG. 4 represents emulsion stability at Day 14 based on emulsions containing components as defined for FIG. 1 but with the higher-boiling additive at a level of 0.5% (w/v) of the emulsion.

[Pluronic F-68=a polyethylene oxide surfactant]

From FIGS. 1 to 4 it can be seen that the higher boiling additive confers improved stability on the emulsions both at 0° C. and 37° C., the effect being most marked for the $C_{16}$ additive (i.e. perfluoroperhydrofluoranthene).

It is also noteworthy that the concentration of the higher boiling additive can also affect stabilization. Thus a 1% level of additive confers greater stability than a 0.5% level of additive.

For emulsion preparations stored at high temperatures of 37° C. (accelerated stability test) a relatively marked increase in stability is observed for emulsions containing the higher boiling point additives. This is strongly apparent for emulsions containing perfluoroperhydrofluoranthene.

The experimental details of preparation and sizing of the emulsions on which the bar charts of FIGS. 1 to 4 are based are as follows:

Perfluorocarbon emulsions were prepared using an ultrasonic homogeniser (Dawe Soniprobe); the experimental conditions were 30 minutes homogenisation at setting 6. Formulations in weight/volume for the emulsion types are listed above.

Emulsions were sized using the photon Correlation Spectroscopy Method (PCS—Malvern Instruments Limited) on preparation, and stored at either a temperature of 0° C. or 37° C. (37° C. constitutes an accelerated stability test). The emulsions were periodically assessed for a relative change in size.

The stability parameter is described as the ratio Dt/Do where Do corresponds to the initial particle size of the formulation and Dt is the size at time t (days). It follows that on the day of initial sizing Dt=Do and the stability parameter will equal 1. An increase in particle size is therefore described by a stability parameter value greater than 1.

The "Absolute Stability" parameter plotted along the vertical axis of the bar charts of FIGS. 1 to 4 is the reciprocal of this stability parameter.

The suitability of the emulsions of the invention for use as blood-substitutes in animals is illustrated by the following biological experimental data.

A 20% w/v emulsion of perfluorodecalin containing 1% high boiling point oil ($C_{16}F_{26}$) was used. Female Wistar rats (body weight: 140-160 g) were injected either intravenously (i.v.) via a tail vein or intraperitoneally (i.p.) with 10 ml.kg$^{-1}$ body weight emulsion which had been prewarmed to about 37° C. Blood samples (about 0.5 ml) were removed from the retro-orbital plexus under light ether anaesthesia on days 0, +3 and +5. On day 7, animals were also anaesthetized with ether and then exsanguinated by cardiac puncture. They were then sacrificed for detailed postmortem and the wet weights of liver, spleen, thymus and mesenteric lymph nodes (MLN) were recorded. Measurements were made of packed cell volume (haematocrit) and 'fluorocrit' on whole blood samples. Additional groups of animal were injected i.v. or i.p. with an identical dose of either Fluosol-DA 20% (Green Cross, Japan) or physiological saline solution (0.9% w/v NaCl) as controls.

All animals survived in an apparently healthy condition throughout the experiments. No fluorocrit was detected in the blood of animals injected with either the emulsion according to the invention or Fluosol-DA. However, the haematocrit decreased slightly in all animals during the course of the experiments. Changes in organ weights occurred in animals injected with the emulsion according to the invention and these were comparable to those seen after administration of Fluosol-DA.

We claim:

1. An oil-in-water emulsion of perfluorodecalin in an aqueous medium, wherein the emulsion is stabilized by the addition of a fluorinated compound of a higher boiling point than perfluorodecalin, wherein the fluorinated compound of higher boiling point is selected from the group consisting of:
   perfluoroperhydrofluorene $C_{13}F_{22}$;
   perfluoroperhydrophenanthrene $C_{14}F_{24}$; and
   perfluoroperhydrofluoranthene $C_{16}F_{26}$;
   and wherein said fluorinated compound of high boiling point is added in an amount of from 0.1% to 5% weight/volume of the emulsion.

2. The emulsion according to claim 1, wherein the fluorinated compound of higher boiling point is added in an amount of from 0.5% to 2% weight/volume of the emulsion.

3. The emulsion according to claim 1, wherein the emulsion is formed with the aid of a surface active agent of the poloxamer type.

4. An oil-in-water emulsion of perfluorodecalin in an aqueous medium, wherein the emulsion is stabilized by the addition of perfluoroperhydrofluoranthene, $C_{16}F_{26}$, added in an amount of from 0.1% to 5% weight volume of the emulsion.

5. A method of stabilizing an oil-in-water emulsion of perfluorodecalin in an aqueous medium, comprising adding to said emulsion a fluorinated compound of a higher boiling point than the perfluorodecalin, wherein the fluorinated compound of higher boiling point is selected from the group consisting of:
   perfluoroperhydrofluorene $C_{13}F_{22}$;
   perfluoroperhydrophenanthrene $C_{14}F_{24}$; and
   perfluoroperhydrofluoranthene $C_{16}F_{26}$;
   and wherein said fluorinated compound of high boiling point is added in an amount of from 0.1% to 5% weight/volume of the emulsion.

6. A method of stabilizing an oil-in-water emulsion of perfluorodecalin in an aqueous medium, comprising adding to said emulsion perfluoroperhydrofluoranthene $C_{16}F_{26}$, in an amount of from 0.1% to 5% weight/volume of the emulsion.

* * * * *